United States Patent
Shah et al.

(10) Patent No.: US 11,298,470 B2
(45) Date of Patent: Apr. 12, 2022

(54) METHODS AND APPARATUS FOR IMPROVED MEDICATION DELIVERY DEVICES

(71) Applicant: ASCENSIA DIABETES CARE HOLDINGS AG, Basel (CH)

(72) Inventors: Nikhil M. Shah, Edison, NJ (US); Eugene R. Prais, West Milford, NJ (US); Nihir Patel, Stamford, CT (US); Jennifer L. Gass, Tarrytown, NY (US); Megan M. Burkarski, Pleasantville, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 145 days.

(21) Appl. No.: 16/345,706

(22) PCT Filed: Oct. 26, 2017

(86) PCT No.: PCT/EP2017/077384
§ 371 (c)(1),
(2) Date: Apr. 27, 2019

(87) PCT Pub. No.: WO2018/077993
PCT Pub. Date: May 3, 2018

(65) Prior Publication Data
US 2019/0351154 A1    Nov. 21, 2019

Related U.S. Application Data

(60) Provisional application No. 62/413,988, filed on Oct. 28, 2016.

(51) Int. Cl.
*A61M 5/50* (2006.01)
*A61M 5/315* (2006.01)

(52) U.S. Cl.
CPC ...... *A61M 5/5086* (2013.01); *A61M 5/31528* (2013.01); *A61M 5/31551* (2013.01);
(Continued)

(58) Field of Classification Search
CPC .................... A61M 5/31528; A61M 5/31551
See application file for complete search history.

(56) References Cited

U.S. PATENT DOCUMENTS

| | | |
|---|---|---|
| 6,352,523 B1 | 3/2002 | Brown et al. |
| 2005/0020987 A1 | 1/2005 | Huang |

(Continued)

FOREIGN PATENT DOCUMENTS

| | | | |
|---|---|---|---|
| EP | 3 058 970 A1 | 8/2016 | |
| EP | 3058970 A1 * | 8/2016 | ............. A61M 5/20 |

(Continued)

OTHER PUBLICATIONS

International Search Report of International Application No. PCT/EP2017/077384 dated Feb. 20, 2018.

(Continued)

*Primary Examiner* — Theodore J Stigell
*Assistant Examiner* — Rachel T. Smith
(74) *Attorney, Agent, or Firm* — Dugan & Dugan, PC

(57) ABSTRACT

Embodiments provide systems, methods, and apparatus for a medication delivery device. The device includes a dose selector for selecting an amount of medication to deliver; a first capacitive sensor adjacent the dose selector and operative to detect linear displacement of the dose selector during medication delivery; a screw coupled to the dose selector; a second capacitive sensor adjacent the screw and operative to detect linear displacement of the screw during medication delivery; and a processor coupled to the first and second capacitive sensors and operative to determine an amount of (Continued)

medication actually delivered by the medication delivery device. Numerous other aspects are provided.

20 Claims, 6 Drawing Sheets

(52) U.S. Cl.
CPC . *A61M 2205/18* (2013.01); *A61M 2205/3317* (2013.01); *A61M 2205/3327* (2013.01); *A61M 2205/3334* (2013.01); *A61M 2205/3368* (2013.01); *A61M 2205/3569* (2013.01); *A61M 2205/3584* (2013.01); *A61M 2205/3592* (2013.01); *A61M 2205/50* (2013.01); *A61M 2205/581* (2013.01); *A61M 2205/584* (2013.01); *A61M 2205/587* (2013.01); *A61M 2230/201* (2013.01)

(56) References Cited

U.S. PATENT DOCUMENTS

| | | | |
|---|---|---|---|
| 2011/0313395 A1* | 12/2011 | Krulevitch | A61M 5/3129 604/504 |
| 2014/0276548 A1* | 9/2014 | Bollish | G16H 20/17 604/503 |
| 2014/0276583 A1 | 9/2014 | Chen et al. | |
| 2015/0190577 A1* | 7/2015 | Shaanan | A61M 5/31585 604/66 |
| 2016/0378951 A1 | 12/2016 | Gofman et al. | |
| 2018/0126083 A1* | 5/2018 | Schmid | A61M 5/326 |

FOREIGN PATENT DOCUMENTS

| | | | | |
|---|---|---|---|---|
| JP | 2004538052 A | 12/2004 | | |
| JP | 2012519028 A | 8/2012 | | |
| JP | 2015502785 A | 1/2015 | | |
| JP | 2015192889 A | 11/2015 | | |
| JP | 2016504116 A | 2/2016 | | |
| WO | WO 2010/098928 | 9/2010 | | |
| WO | WO-2015001008 A1 * | 1/2015 | ........ | A61M 5/31568 |
| WO | WO 2015/138093 A2 | 9/2015 | | |
| WO | WO-2016059616 A1 * | 4/2016 | ............. | G16H 20/17 |

OTHER PUBLICATIONS

Search Report of related Chinese Application No. 201780074341.5 dated Dec. 4, 2020.
International Preliminary Report on Patentability of International Application No. PCT/EP2017/077384 dated May 9, 2019.

* cited by examiner

METHODS AND APPARATUS FOR IMPROVED MEDICATION DELIVERY DEVICES

CROSS REFERENCE TO RELATED APPLICATION

This claims priority to U.S. Provisional Patent Application No. 62/413,988, filed Oct. 28, 2016, which is hereby incorporated by reference herein in its entirety for all purposes.

FIELD

The invention relates to medication delivery devices, and more specifically to apparatus, systems, and methods for improved medication delivery devices.

BACKGROUND

Many different medication delivery devices and physiological fluid analyte monitoring systems are commercially available. A common application of such devices is the infusion of insulin to and the monitoring of blood glucose levels of diabetic patients. Increased portability and ease of use of such devices have enabled diabetic patients to administer a self-regulated medical treatment regime which in turn provides an increased level of patient autonomy and privacy. This is particularly beneficial since diabetic patients' glucose levels may vary daily or hourly.

Such self-regulated diabetic treatment regimens often include the self-administration, either by injection and/or ingestion, of various medications, e.g., insulin. In addition to a high degree of medication compliance, for such self-regulated regimes to work effectively and safely, the patient is required to closely monitor the dosage and times at which medication is taken and may need to record or document corresponding medically relevant self-monitoring information, e.g., blood glucose level, insulin dosage, etc. The monitoring of such data helps to determine the current status and course of action (e.g., regimen change) of future actions. Because the recordation of this information can be time consuming and inconvenient, particularly if done with pen and paper, it is desirable that recordation, compilation and tracking of this type of information be minimized and as time-efficient for the patient as possible.

Accordingly, there is continued interest in the development of improved devices and methods for the patient-regulated administration of medication and associated monitoring and recordation of medical information, including but not limited to drug administration (e.g., injection) time and dosage, analyte concentration (e.g., glucose levels, etc.). Of particular interest would be the development of a patient-controlled medication administration and monitoring system which provides the patient with flexibility and control; increases reliability, accuracy, convenience, privacy and ease of use for the patient; and enhances portability of system components. Thus, what are needed are systems, apparatus, and methods for improved medication delivery devices.

SUMMARY

In some aspects, embodiments of the invention provide an apparatus for automatically tracking an administered dosage of a medication delivery device. An example medication delivery device includes a dose selector for selecting an amount of medication to deliver; a first capacitive sensor adjacent the dose selector and operative to detect linear displacement of the dose selector during medication delivery; a transceiver; and a processor coupled to the first capacitive sensor and to the transceiver and operative to determine an amount of medication actually delivered by the medication delivery device based on the detected linear displacement of the dose selector and further operative to communicate via the transceiver the determined amount of medication from the medication delivery device to a data management system or a blood glucose meter.

According to another aspect, a method of delivering a medication with a medication delivery device is provided. The method includes selecting an amount of medication to deliver via a dose selector; detecting linear displacement of the dose selector during medication delivery via a first capacitive sensor adjacent the dose selector; detecting linear displacement of a screw coupled to the dose selector during medication delivery via a second capacitive sensor adjacent the screw; and determining an amount of medication actually delivered by the medication delivery device via a processor coupled to the first and second capacitive sensors.

Numerous other aspects are provided in accordance with these and other aspects of the invention. Other features and aspects of the invention will become more fully apparent from the following detailed description, the appended claims and the accompanying drawings.

DESCRIPTION

Figure 1:
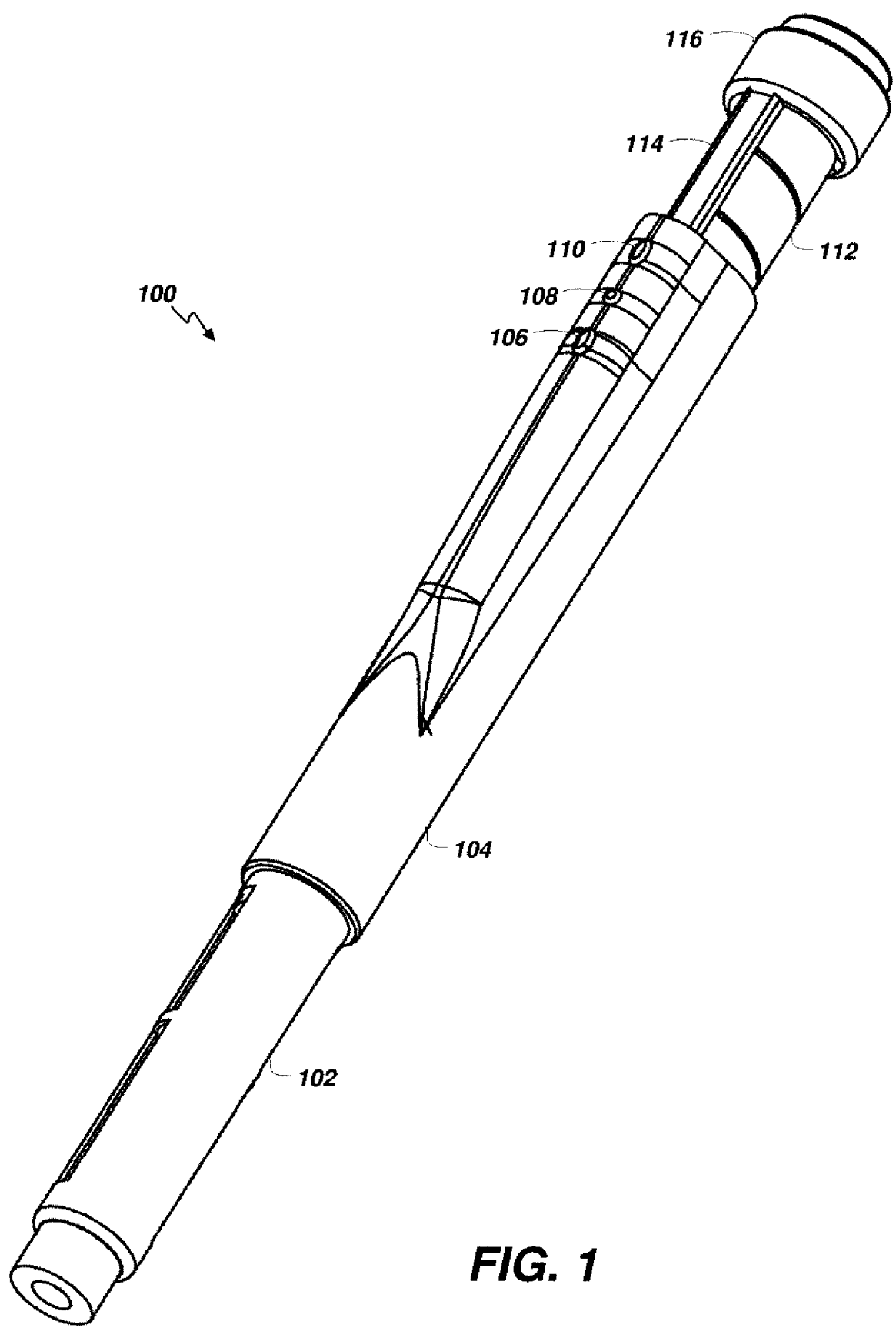
FIG. 1 is an isometric view of an improved medication delivery device according to embodiments of the invention.

For the purposes of promoting an understanding of the principles of embodiments of the invention, reference will now be made to the examples illustrated in the drawings and specific language will be used to describe the same. It will nevertheless be understood that no limitation of the scope of the invention is thereby intended, and any alterations and further modifications in the illustrated embodiments, and any further applications of the principles of the invention as illustrated therein as would normally occur to one skilled in the art to which the invention relates are contemplated herein.

Embodiments of the invention provide enhancements to medication delivery devices intended to be used by patients for self-administration of medication (e.g., insulin). In some embodiments, an improved medication delivery device is provided that is operable to (1) automatically track dose amount information, administration time information, and other information and (2) automatically convey the information via a wireless protocol (e.g., RF/Bluetooth™) to a data management system (DMS) embodied as an application (e.g., a diabetes management application (DMA)) executing on, for example, a smartphone or computer. The improved medication delivery device can also receive information wirelessly from the DMS, e.g., error messages, status messages, and/or commands such as activate a buzzer and/or status light emitting diodes (LEDs).

In some embodiments, a user can manually operate a mechanical dose selector of the improved medication delivery device to dial-in a dose by rotating the dose selector (e.g., coupled to an internal screw) to the desired amount. Administration is effected by pressing the cap which allows a plunger to apply pressure to a medication cartridge to administer the selected dose through a needle.

In some embodiments, the delivery device uses a capacitive sensor to measure the linear displacement of the dose selector after the cap is pressed. In some embodiments, the device uses a capacitive sensor to measure the linear displacement of the screw and therefore the displacement of the plunger. In some embodiments, the device uses capacitive sensors to measure the linear displacements of both the dose selector and the screw. In any case, the device can also record the time and date that the dose was administered as well as the rate at which the dose was administered. Embodiments of the invention also include a reusable medication cartridge holder with one or more capacitive sensors. In some embodiments, a thermal sensor is included within the device, mounted, for example, on the circuit board of the device.

A processor coupled to a clock and memory is operative to store various information from multiple sensors in addition to those mentioned above. For example, the processor can store information about the needle (e.g., time and date the needle was removed or installed in the device), the medication (e.g., time and date the medication cartridge was installed or changed), and the ambient temperatures that the device (and any installed medication cartridge) was exposed to as detected by the thermal sensor. In some embodiments, the device is operative to use a transceiver coupled to the processor to wirelessly communicate with a data management system (e.g., a diabetes management application). The device can send the information about the device usage (e.g., the dose administration), the needle, the medication, the temperatures, etc. to the DMA and/or to an analyte monitoring system (e.g., a blood glucose meter) or other health data manager device (e.g., smart phone, tablet, PC, wrist computer, etc.).

Figure 2:
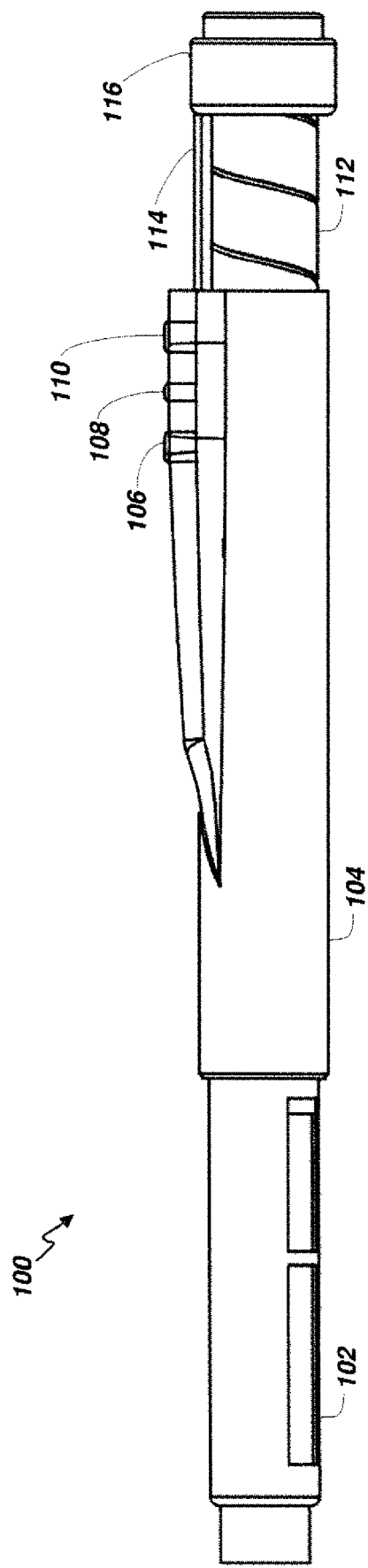
FIG. 2 is a plan view of an improved medication delivery device according to embodiments of the invention.
Figure 3A:
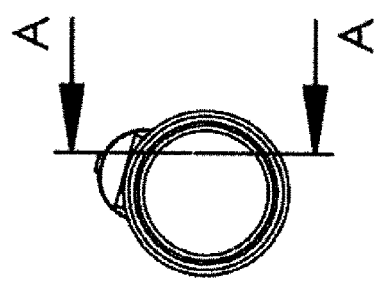
FIG. 3A is an end view of an improved medication delivery device according to embodiments of the invention.
Figure 3B:
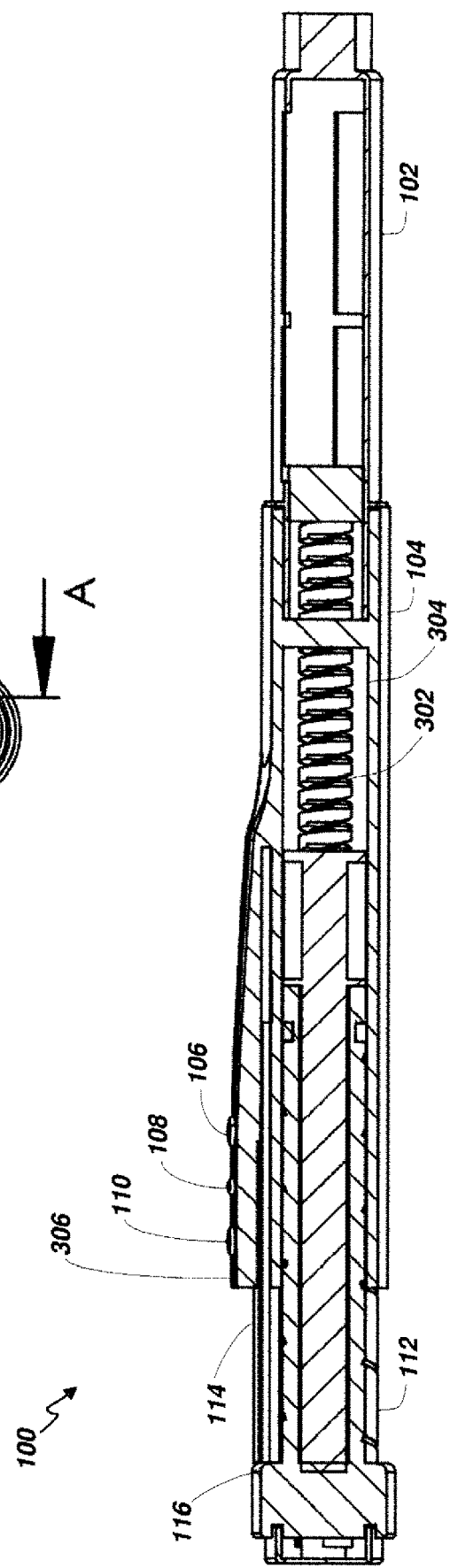
FIG. 3B is a side cross-sectional view of the improved medication delivery device of FIG. 3A taken along the line A-A.
Figure 4:
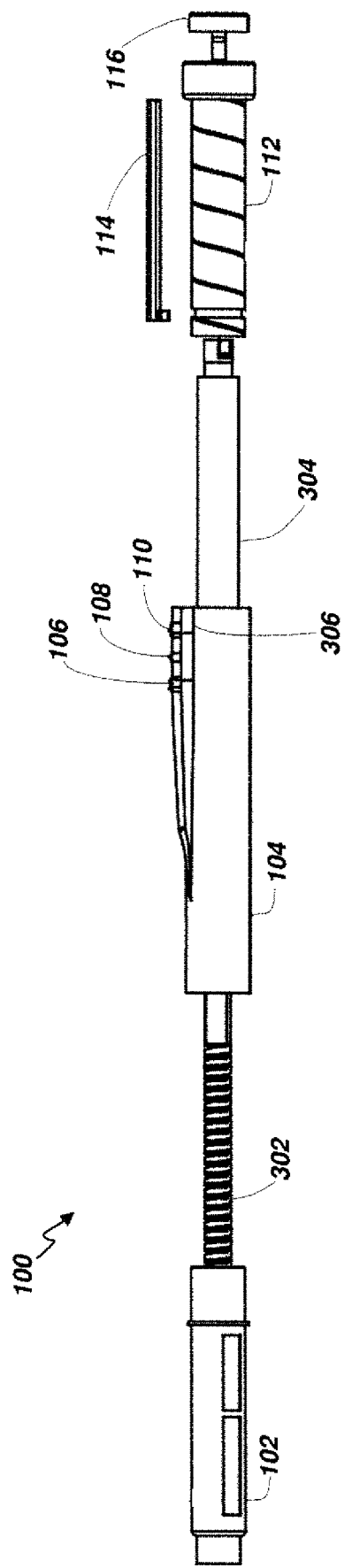
FIG. 4 is an exploded plan view of an improved medication delivery device according to embodiments of the invention.

Turning now to FIGS. 1 through 4, an isometric view of an example improved medication delivery device 100 according to embodiments of the invention is depicted in FIG. 1. FIG. 2 is a plan view of the example device 100. FIG. 3A is an end view and FIG. 3B is a side cross-sectional view of the example device 100 taken along line A-A. FIG. 4 is an exploded plan view of the example device 100. The example device 100 includes a medication cartridge holder 102 that can be detachably coupled to a device body 104. The device body 104 can include a power button 106, an LED indicator 108, and a control (e.g., set) button 110. Extending from the device body 104 is a dose selector 112. A follower 114 with a stator track below a dose scale (i.e., a capacitive sensor) is mounted adjacent the dose selector 112. The cap 116 is attached at the end of the dose selector 112.

As more clearly shown in FIGS. 3B and 4, the screw 302 is disposed within a screw housing 304, and a circuit board is contained within a circuit board housing 306. Other configurations are possible. For example, in addition to the follower 114 on the dose selector, a second follower and capacitive sensor can be provided on/adjacent the screw 302 which can more directly measure the dose administered.

Figure 5:
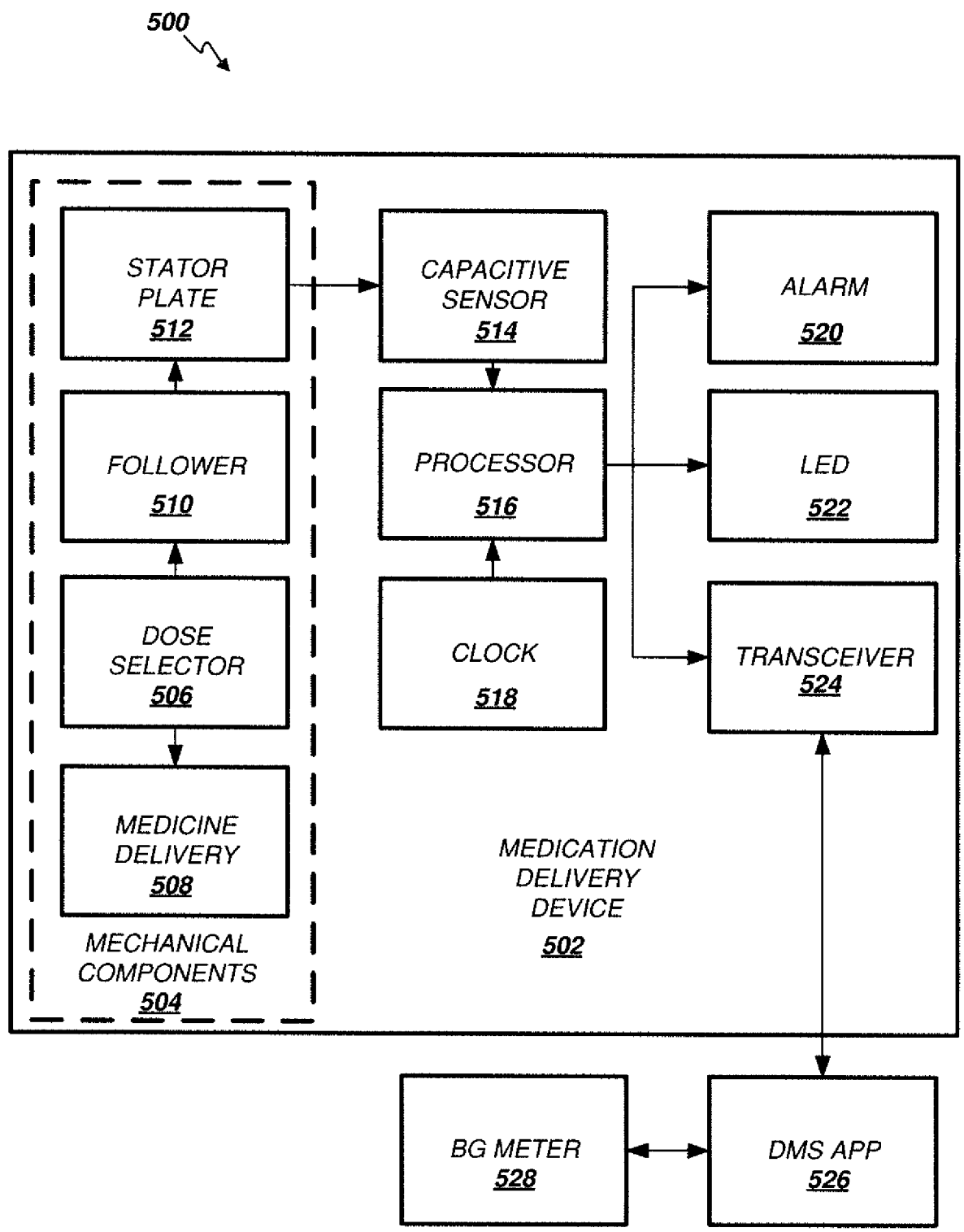
FIG. 5 is a block diagram depicting an example of a system architecture according to embodiments of the invention.

Turning now to FIG. 5, a block diagram depicting an example of a system architecture 500 is depicted. The medication delivery device 502 can include various mechanical components 504 such as a dose selector 506 which drives both the medicine delivery components 508 (e.g., the screw 302, the medication cartridge, etc.) and the follower 510. The stator plate 512 on the follower 510 moves past the capacitive sensor 514 which can send signals to the processor 516 indicating the amount of movement of the dose selector 506. Combined with time information from the clock 518, the processor 516 can determine both the time of the administration of the medication and the rate at which it was delivered. In some embodiments, the processor 516 can also be coupled to an alternative or additional capacitive sensor disposed proximate to the screw 302 to measure the dose administered more directly and more accurately. The processor 516 is also coupled to a memory (not shown), an alarm 520 (e.g., an audible buzzer or other sound generation device), a status indicator LED 522, and a transceiver 524 (e.g., a radio frequency (RF) transmitter/receiver such as a Bluetooth™ transceiver). The transceiver 524 allows communication of information generated by the processor 516 from, for example, the capacitive sensor 514 and clock 518, to a DMS application 526 and/or to a BG meter 528. Likewise, information (e.g., status information, control commands, etc.) can be communicated to the processor 516 via the transceiver 524.

In some embodiments, the DMS application 526 can include a data structure (e.g., a database, a hierarchy of objects, a software architecture) adapted to support the functions described above and to store information.

Figure 6:
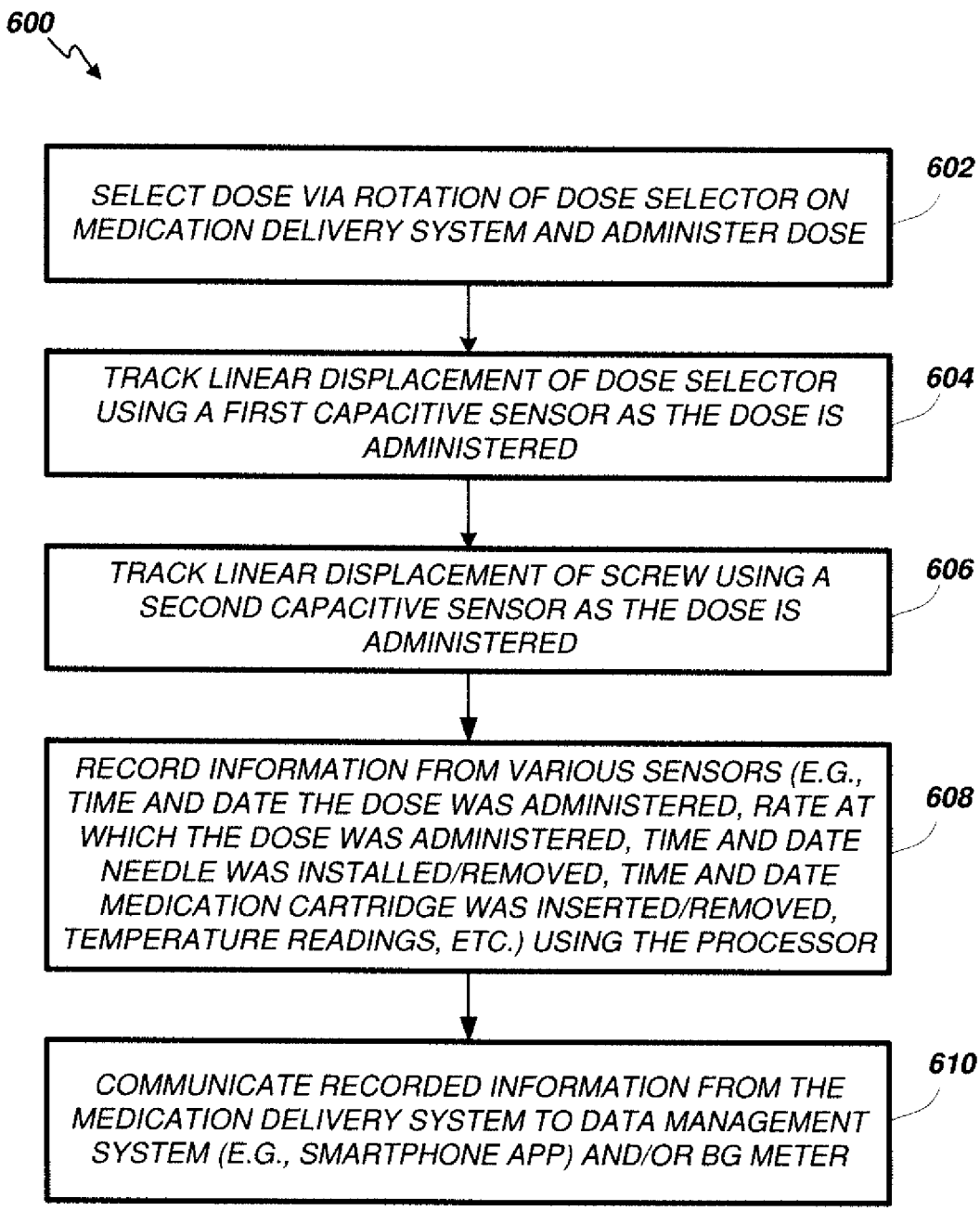
FIG. 6 is a flowchart depicting an example method according to embodiments of the invention.

Turning now to FIG. 6, an example method 600 according to embodiments of the invention is illustrated in a flowchart. Although a particular order of steps is shown, the example method 600 can be performed in any practicable order. In addition, although a specific number of steps are shown, the example method 600 can include additional, alternative, or fewer steps. The user selects a dose by rotating the dose selector of the medication delivery device and then administers the medication by pressing the cap (602). In some embodiments, linear displacement of the dose selector is tracked using a first capacitive sensor as the dose is administered (604). In some embodiments, linear displacement of the screw is tracked using a second capacitive sensor as the dose is administered (606). The processor stores information from the sensors (608). In some embodiments, in addition to the capacitive sensors on the dose selector and screw that can provide two independent measurements of medication administration including rate of delivery information, other sensors can be included that allow capture of additional information such as the time and date that a needle was installed/removed, the time and date that a medication cartridge was inserted/removed, and ambient temperature readings. The stored information can be communicated to a data management system such as a diabetes management application executing on a smartphone and/or to a BG meter (610).

Embodiments of the invention help to seamlessly and automatically collect important diabetes management data with minimal or no input from the user. In addition, various embodiments reduce the possibility for error by the user during medication dose administration, eliminate the need to record medication dose data manually, ease the burden on the user, reduce the possibility of using expired medication relative to the initial opening of a medication cartridge, monitor the accuracy of the mechanical system in the delivery device, enable methods to monitor proper rate of dose administration, coach the user regarding the proper rate of delivery, provide a more accurate means of selecting a dose, ensure proper needle use, ensure needles are primed before actual administration, allow location of a misplaced medication delivery device to be determined using the wireless transceiver feature (e.g., by sensing the device within Bluetooth™ range), ensure the device has been stored within an allowable temperature range, allow for monitoring and coaching of the prescribed insulin regimen, and inform the user's healthcare provider (HCP) of actual diabetes management activity by the user (e.g., via the DMA).

Embodiments of the invention solve a number of problems. These problems include:

(A) No expiration dates are typically listed for conventional reusable medication delivery devices. Should there be mechanical wear over time or other failures, such as extreme heat, the accuracy of the insulin pen can decrease and dose administration can be outside allowable limits.

(B) Conventional insulin pens do not allow patients to administer a dose less than single or half unit increments.

(C) Insulin cartridges that have been opened have a usable time period of 30 days from opening. After 30 days, the insulin is no longer allowed to be administered, regardless of the amount of insulin left in the cartridge. This can be easily forgotten by patients and can result in expired insulin being injected into the user.

(D) The current automatic delivery insulin pens (e.g., the FlexTouch model by Novo Nordisk) average maximum injection speed is higher than the manual application. For example, the FlexTouch has an average maximum flow rate of 15.61 units/sec whereas a manual application is in the 640 units/sec range. The flow rate of insulin delivery is a key element that determines the comfort of pen use. As result, the higher rate of delivery of the auto-injection devices is assumed to deliver more turbulent fluid flow into the patient and a relatively painful experience. The design of conventional insulin pens incorporate mechanisms which make it difficult for users to control and monitor injection rate.

(E) It is recommended that insulin pen needles be changed every dose and stored with no needle attached. This ensures that needles are sterile, leaks are prevented, air bubbles are kept out, and needles are prevented from getting clogged. Users can forget to do this.

(F) Priming ensures that there is no air in the needle and there is no gap between the screw and plunger after a cartridge change. Users can forget to prime.

(G) Insulin pens are pocket sized items that can be misplaced or forgotten to be taken. A person leaving for work can forget an insulin pen at home, or can leave his or her pen at work before coming home. Insulin pens can also be misplaced within Bluetooth range, such as in a car or purse.

(H) Insulin pens and open cartridges must always be kept at room temperature, and should be kept away from extreme temperatures such as in a hot car or refrigerator. Changes in volume of the insulin can cause leaks and/or changes in the strength of the dose due to concentration changes.

(I) Errors can be made by patients who take a dose different than the one prescribed by the doctor. Furthermore, doses can be missed.

(J) Doctors give patients information about diabetes care. This includes an insulin regimen. Doctors cannot easily verify if the instructions are being followed.

The above-listed problems are addressed by embodiments of the invention as follows:

(A) Comparing the dose selected to the actual dose administered can ensure confidence in the device and, if a discrepancy is detected, alert a user that the device is no longer operating accurately. A capacitive displacement sensor on both the screw and dose selector can track dose amount and time, which can be sent to the DMA to be compared. Any variation greater than the allowable limits will set off an alert.

(B) Using a capacitive sensor can allow a dose to be set to within smaller than single or half unit increments. This can be useful for patients who are sensitive to insulin.

(C) Alerting the user that the cartridge has been on the device for longer than 30 days reminds the user that the insulin currently in the device is no longer usable. A capacitive touch film or mechanical switch can record when there is a cartridge installed and when it is removed to replace the cartridge. A clock on the circuit board coupled to the processor can track how long it has been since the last replacement. An LED indicator and/or alert on a paired phone can remind the user that the insulin is expired.

(D) Insulin delivery devices should provide a means for users to track and manually control their injection speeds in real time adjusting accordingly. A capacitive sensor is able to detect real time displacement. Couple that with the timing function of the processor, and the velocity (speed) is able to be calculated. The feedback can be outputted in real-time to either the device's indicator lights, display, buzzer, vibratory motor or display screen on the DMA. In this way, the user is able to visually, audibly, and/or tactilely be coached to deliver medication at an optimal rate so that the delivery experience becomes optimal in the sense of comfort. Furthermore, the rates can be collected over time and stored in the DMA to provide analytical insights (e.g., patient specific medication delivery rates per injection site) into the user's medication delivery regime. Medication administration may thus be made more comfortable.

(E) Alerting the user that the device was stored with the needle after an injection reminds the user to remove it. If the needle is still not removed, another alarm will alert the user when he or she is setting the next dose that the needle currently on the device is old. A capacitive touch film or mechanical switch can record when there is a needle installed and when it is removed. An LED indicator and/or alert on a paired phone (e.g., running the DMA) can remind the user that the insulin is expired.

(F) Alerting a user trying to set a dose higher than two units can be a reminder that a prime shot needs to be performed before every dose. For example, an LED indicator on the device can turn a certain color (e.g., red) when the first dose being dialed is greater than two units. A change of a needle and a dose set higher than two units will also trigger the indicator.

(G) Alerting the user when the device is no longer paired to the user's phone can remind the user that the insulin pen is not with them. For example, Bluetooth™ pairing termination that is not manually done can set off an alert on the user's phone that the device is not with them. For pens in Bluetooth™ range, using the DMA on the paired phone can set off an audible or visual indicator on the device. When a device is in Bluetooth™ range, it can be seen or heard by an LED on it or a speaker in it.

(H) Alerting the user that the device has been exposed to extreme temperatures can allow the user to dispose of a pen that is no longer usable. A temperature sensor, such as a thermistor, can record temperatures intermittently and when paired with the phone, and can alert the user that the device is no longer usable. An LED indicator can also alert the user before a dose.

(I) Alerting the user that the dose currently set is not the dose meant to be taken can allow the user to double check the dose and set the correct one. A missed dose can set off a reminder for the user. For example, the DMA can contain the dose regimen and compare it to actual values from the device. Any instance of doses not matching or missed doses will set off an alarm.

(J) Sending all information from the DMA to the HCP can inform the HCP of all aspects of medication use. All information sent to the DMA from the device can be sent to the HCP, who can then review the information to make sure that the user is correctly taking medication as prescribed. Thus, A Bluetooth™ enabled pen that tracks both dose amount and time information can be useful for diabetes care management. This information can be used to monitor medication delivery device (e.g., an insulin pen) accuracy (A), reduce the possibility of expired insulin use (B), monitor speed of dose administration (C), provide a more accurate way to select a dose (D), ensure proper needle use (E), ensure prime shots are used (F), locate a misplaced pen within Bluetooth™ range (G), ensure the device has been kept within allowable temperature range (H), monitor and coach the prescribed insulin regimen (I), and inform the HCP of the actual diabetes management of the patient (J).

Numerous embodiments are described in this disclosure, and are presented for illustrative purposes only. The described embodiments are not, and are not intended to be, limiting in any sense. The disclosed invention is widely applicable to numerous embodiments, as is readily apparent from the disclosure. One of ordinary skill in the art will recognize that the disclosed invention may be practiced with various modifications and alterations, such as structural, logical, software, and electrical modifications. Although particular features of the disclosed invention may be described with reference to one or more particular embodiments and/or drawings, it should be understood that such features are not limited to usage in the one or more particular embodiments or drawings with reference to which they are described, unless expressly specified otherwise.

This disclosure is neither a literal description of all embodiments nor a listing of features of the invention that must be present in all embodiments.

The title (set forth at the beginning of the first page of this disclosure) is not to be taken as limiting in any way as to the scope of the disclosed invention.

The term "product" means any machine, manufacture and/or composition of matter as contemplated by 35 U.S.C. § 101, unless expressly specified otherwise.

Each process (whether called a method, class behavior, algorithm or otherwise) inherently includes one or more steps, and therefore all references to a "step" or "steps" of a process have an inherent antecedent basis in the mere recitation of the term 'process' or a like term. Accordingly, any reference in a claim to a 'step' or 'steps' of a process has sufficient antecedent basis.

When an ordinal number (such as "first", "second", "third", and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

When a single device, component, structure, or article is described herein, more than one device, component, structure or article (whether or not they cooperate) may alternatively be used in place of the single device, component or article that is described. Accordingly, the functionality that is described as being possessed by a device may alternatively be possessed by more than one device, component or article (whether or not they cooperate).

Similarly, where more than one device, component, structure, or article is described herein (whether or not they cooperate), a single device, component, structure, or article may alternatively be used in place of the more than one device, component, structure, or article that is described. For example, a plurality of computer-based devices may be substituted with a single computer-based device. Accordingly, the various functionality that is described as being possessed by more than one device, component, structure, or article may alternatively be possessed by a single device, component, structure, or article.

The functionality and/or the features of a single device that is described may be alternatively embodied by one or more other devices that are described but are not explicitly described as having such functionality and/or features. Thus, other embodiments need not include the described device itself, but rather can include the one or more other devices which would, in those other embodiments, have such functionality/features.

Devices that are in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for weeks at a time. In addition, devices that are in communication with each other may communicate directly or indirectly through one or more intermediaries.

A description of an embodiment with several components or features does not imply that all or even any of such components and/or features are required. On the contrary, a variety of optional components are described to illustrate the wide variety of possible embodiments of the present invention(s). Unless otherwise specified explicitly, no component or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

Although a process may be described as including a plurality of steps, that does not indicate that all or even any of the steps are essential or required. Various other embodiments within the scope of the described invention(s) include other processes that omit some or all of the described steps. Unless otherwise specified explicitly, no step is essential or required.

Although a product may be described as including a plurality of components, aspects, qualities, characteristics and/or features, that does not indicate that all of the plurality are essential or required. Various other embodiments within the scope of the described invention(s) include other products that omit some or all of the described plurality.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA" does not imply that any or all of the three items of that list are mutually exclusive and does not imply that any or all of the three items of that list are comprehensive of any category.

Headings of sections provided in this disclosure are for convenience only, and are not to be taken as limiting the disclosure in any way.

"Determining" something can be performed in a variety of manners and therefore the term "determining" (and like terms) includes calculating, computing, deriving, looking up (e.g., in a table, database or data structure), ascertaining, recognizing, associating, and the like.

A "display" as that term is used herein is an area that conveys information to a viewer. The information may be dynamic, in which case, an LCD, LED, CRT, Digital Light Processing (DLP), rear projection, front projection, or the like may be used to form the display.

This disclosure may refer to a "control system", application, or program. A control system, application, or program, as that term is used herein, may be a computer processor coupled with an operating system, device drivers, and appropriate programs (collectively "software") with instructions to provide the functionality described for the control system. The software is stored in an associated memory device (sometimes referred to as a computer readable medium). While it is contemplated that an appropriately programmed general purpose computer or computing device may be used, it is also contemplated that hard-wired circuitry or custom hardware (e.g., an application specific integrated circuit (ASIC)) may be used in place of, or in combination with, software instructions for implementation of the processes of various embodiments. Thus, embodiments are not limited to any specific combination of hardware and software.

A "processor" means any one or more microprocessors, Central Processing Unit (CPU) devices, computing devices, microcontrollers, digital signal processors, or like devices. Exemplary processors are the INTEL PENTIUM or AMD ATHLON processors.

The term "computer-readable medium" refers to any statutory medium that participates in providing data (e.g., instructions) that may be read by a computer, a processor or a like device. Such a medium may take many forms, including but not limited to non-volatile media, volatile media, and specific statutory types of transmission media. Non-volatile media include, for example, optical or magnetic disks and other persistent memory. Volatile media include DRAM, which typically constitutes the main memory. Statutory types of transmission media include coaxial cables, copper wire and fiber optics, including the wires that comprise a system bus coupled to the processor. Common forms of computer-readable media include, for example, a floppy disk, a flexible disk, hard disk, magnetic tape, any other magnetic medium, a CD-ROM, Digital Video Disc (DVD), any other optical medium, punch cards, paper tape, any other physical medium with patterns of holes, a RAM, a PROM, an EPROM, a FLASH-EEPROM, a USB memory stick, a dangle, any other memory chip or cartridge, a carrier wave, or any other medium from which a computer can read. The terms "computer-readable memory" and/or "tangible media" specifically exclude signals, waves, and wave forms or other intangible or non-transitory media that may nevertheless be readable by a computer.

Various forms of computer readable media may be involved in carrying sequences of instructions to a processor. For example, sequences of instruction (i) may be delivered from RAM to a processor, (ii) may be carried over a wireless transmission medium, and/or (iii) may be formatted according to numerous formats, standards or protocols. For a more exhaustive list of protocols, the term "network" is defined below and includes many exemplary protocols that are also applicable here.

It will be readily apparent that the various methods and algorithms described herein may be implemented by a control system and/or the instructions of the software may be designed to carry out the processes of the present invention.

Where databases and/or data structures are described, it will be understood by one of ordinary skill in the art that (i) alternative database structures to those described may be readily employed, and (ii) other memory structures besides databases may be readily employed. Any illustrations or descriptions of any sample databases/data structure presented herein are illustrative arrangements for stored representations of information. Any number of other arrangements may be employed besides those suggested by, e.g., tables illustrated in drawings or elsewhere. Similarly, any illustrated entries of the databases represent exemplary information only; one of ordinary skill in the art will understand that the number and content of the entries can be different from those described herein. Further, despite any depiction of the databases as tables, other formats (including relational databases, object-based models, hierarchical electronic file structures, and/or distributed databases) could be used to store and manipulate the data types described herein. Likewise, object methods or behaviors of a database can be used to implement various processes, such as those described herein. In addition, the databases may, in a known manner, be stored locally or remotely from a device that accesses data in such a database. Furthermore, while unified databases may be contemplated, it is also possible that the databases may be distributed and/or duplicated amongst a variety of devices.

As used herein a "network" generally refers to an information or computing network that can be used to provide an environment wherein one or more computing devices may communicate with one another. Such devices may communicate directly or indirectly, via a wired or wireless medium such as the Internet, LAN, WAN or Ethernet (or IEEE 802.3), Token Ring, or via any appropriate communications means or combination of communications means. Exemplary protocols include but are not limited to: Bluetooth™, Time Division Multiple Access (TDMA), Code Division Multiple Access (CDMA), Global System for Mobile communications (GSM), Enhanced Data rates for GSM Evolution (EDGE), General Packet Radio Service (GPRS), Wideband CDMA (WCDMA), Advanced Mobile Phone System (AMPS), Digital AMPS (D-AMPS), IEEE 802.11 (WI-FI), IEEE 802.3, SAP, the best of breed (BOB), system to system (S2S), or the like. Note that if video signals or large files are being sent over the network, a broadband network may be used to alleviate delays associated with the transfer of such large files, however, such is not strictly required. Each of the devices is adapted to communicate on such a communication means. Any number and type of machines may be in communication via the network. Where the network is the Internet, communications over the Internet may be through a website maintained by a computer on a remote server or over an online data network including commercial online service providers, bulletin board systems, and the like. In yet other embodiments, the devices may communicate with one another over RF, cable TV, satellite links, and the like. Where appropriate, encryption or other security measures such as logins and passwords may be provided to protect proprietary or confidential information.

Communication among computers and devices may be encrypted to insure privacy and prevent fraud in any of a variety of ways well known in the art. Appropriate cryptographic protocols for bolstering system security are described in Schneier, APPLIED CRYPTOGRAPHY, PROTOCOLS, ALGORITHMS, AND SOURCE CODE IN C, John Wiley & Sons, Inc. 2d ed., 1996, which is incorporated by reference in its entirety.

It will be readily apparent that the various methods and algorithms described herein may be implemented by, e.g., appropriately programmed, general purpose computers and computing devices. Typically a processor (e.g., one or more microprocessors) will receive instructions from a memory or like device, and execute those instructions, thereby performing one or more processes defined by those instructions. Further, programs that implement such methods and algorithms may be stored and transmitted using a variety of media (e.g., computer readable media) in a number of manners. In some embodiments, hard-wired circuitry or custom hardware may be used in place of, or in combination with, software instructions for implementation of the processes of various embodiments. Thus, embodiments are not limited to any specific combination of hardware and software. Accordingly, a description of a process likewise describes at least one apparatus for performing the process, and likewise describes at least one computer-readable medium and/or memory for performing the process. The apparatus that performs the process can include components and devices (e.g., a processor, input and output devices) appropriate to perform the process. A computer-readable medium can store program elements appropriate to perform the method.

This disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicant intends to file additional applications to pursue patents for subject matter that has been disclosed and enabled but not claimed in the present application.

The foregoing description discloses only exemplary embodiments of the invention. Modifications of the above disclosed apparatus and methods that fall within the scope of the invention will be readily apparent to those of ordinary skill in the art. For example, although the examples discussed above are illustrated for a healthcare market, embodiments of the invention can be implemented for other markets.

Accordingly, while the invention has been disclosed in connection with exemplary embodiments thereof, it should be understood that other embodiments may fall within the spirit and scope of the invention, as defined by the following claims.

The invention claimed is:

1. A medication delivery device comprising:
   a dose selector for selecting an amount of medication to deliver;
   a first capacitive sensor adjacent the dose selector and operative to detect linear displacement of the dose selector during medication delivery;
   a screw coupled to the dose selector;
   a second capacitive sensor adjacent the screw and operative to detect linear displacement of the screw during medication delivery;
   a transceiver; and
   a processor coupled to the first capacitive sensor, the second capacitive sensor, and the transceiver and operative to determine an amount of medication actually delivered by the medication delivery device based on a comparison of determined amounts of medication via the detected linear displacement of the dose selector and the detected linear displacement of the screw, wherein a variation in the determined amounts of medication greater than a predetermined limit sets off an alert to a user that the medication delivery device is no longer operating accurately, the processor further operative to communicate via the transceiver the determined amount of medication from the medication delivery device to a data management system or a blood glucose meter.

2. The medication delivery device of claim 1, wherein the dose selector is rotatable for selecting an amount of medication to deliver.

3. The medication delivery device of claim 1, wherein the processor is operative to record information related to the determined amount of medication.

4. The medication delivery device of claim 3, wherein the information related to the determined amount of medication includes at least one of:
   a time and date a dose was administered;
   a rate at which the dose was administered;
   a time and date a needle of the medication delivery device was installed or removed;
   a time and date a medication cartridge of the medication delivery device was inserted or removed; and
   a temperature reading.

5. The medication delivery device of claim 3, wherein the processor is further operative via the transceiver to communicate the recorded information from the medication delivery device to the data management system or the blood glucose meter.

6. The medication delivery device of claim 1, further comprising an indicator, wherein the processor is operative to activate the indicator in response to at least one of an improper amount of medication having been delivered by the medication delivery device or a needle of the medication delivery device requiring replacement.

7. The medication delivery device of claim 6, wherein the indicator comprises a sound generation device or an LED.

8. The medication delivery device of claim 1, wherein the transceiver comprises a radio frequency transceiver or a Bluetooth® transceiver.

9. The medication delivery device of claim 1, further comprising a clock coupled to the processor.

10. The medication delivery device of claim 1, further comprising a follower with a stator track mounted adjacent the dose selector, wherein the first capacitive sensor detects linear displacement of the dose selector during medication delivery via a stator plate on the follower moving past the first capacitive sensor.

11. The medication delivery device of claim 1, further comprising a device body and a medication cartridge holder, wherein the medication cartridge holder is reusable, detachably coupled to the device body, and comprises the second capacitive sensor.

12. The medication delivery device of claim 1, further comprising a circuit board housing having a circuit board therein and a thermal sensor mounted on the circuit board.

13. The medication delivery device of claim 12, wherein the processor is further operative to record ambient temperatures that the medication delivery device is exposed to as detected by the thermal sensor.

14. The medication delivery device of claim 13, further comprising an indicator, wherein the processor is further operative to activate the indicator in response to the medication delivery device being exposed to an extreme temperature as detected by the thermal sensor.

15. The medication delivery device of claim 14, wherein the indicator comprises an LED.

16. A method of delivering a medication with a medication delivery device comprising:
    selecting an amount of medication to deliver via a dose selector;
    detecting linear displacement of the dose selector during medication delivery via a first capacitive sensor adjacent the dose selector;
    detecting linear displacement of a screw coupled to the dose selector during medication delivery via a second capacitive sensor adjacent the screw; and
    determining an amount of medication actually delivered by the medication delivery device via a processor coupled to the first and second capacitive sensors based on a comparison of determined amounts of medication via the detected linear displacement of the dose selector and the detected linear displacement of the screw, wherein a variation in the determined amounts of medication greater than a predetermined limit sets off an alert to a user that the medication delivery device is no longer operating accurately.

17. The method of claim 16, wherein the selecting comprises rotating the dose selector to select an amount of medication to deliver.

18. The method of claim 16, further comprising recording information from various sensors using the processor.

19. The method of claim 18, wherein the recording of information comprises recording at least one of:
    a time and date a dose was administered;
    a rate at which the dose was administered;
    a time and date a needle of the medication delivery device was installed or removed;
    a time and date a medication cartridge of the medication delivery device was inserted or removed; and
    a temperature reading.

20. The method of claim 18, further comprising communicating the recorded information from the medication delivery device to a data management system or a blood glucose meter.

* * * * *